United States Patent [19]
Engelhardt et al.

[11] Patent Number: 6,150,666
[45] Date of Patent: Nov. 21, 2000

[54] POLYFOCAL REPRESENTATION OF THE SURFACE PROFILE OF ANY GIVEN OBJECT

[75] Inventors: Johann Engelhardt, Bad Schoenborn; Thomas Zapf, Speyer; Heinrich Ulrich, Heidelberg, all of Germany

[73] Assignee: Leica Microsystems Heidelberg GmbH, Heidelberg, Germany

[21] Appl. No.: 09/319,245

[22] PCT Filed: Dec. 5, 1997

[86] PCT No.: PCT/DE97/02851

§ 371 Date: Jun. 7, 1999

§ 102(e) Date: Jun. 7, 1999

[87] PCT Pub. No.: WO98/25171

PCT Pub. Date: Jun. 11, 1998

[30] Foreign Application Priority Data

Dec. 5, 1996 [DE] Germany .................. 196 50 391

[51] Int. Cl.⁷ .................................................. G01N 21/86
[52] U.S. Cl. .................. 250/559.22; 250/559.4; 250/216
[58] Field of Search ............. 250/559.22, 559.4, 250/208.1, 207.5, 216; 356/376, 378; 396/124, 79, 80, 82

[56] References Cited

U.S. PATENT DOCUMENTS

| 4,484,079 | 11/1984 | Betz et al. | 250/548 |
|---|---|---|---|
| 5,248,876 | 9/1993 | Kerstens et al. | |
| 5,526,338 | 6/1996 | Hasman et al. | 369/112 |

FOREIGN PATENT DOCUMENTS

| 327 425 | 8/1989 | European Pat. Off. |
| 0 623 804 A2 | 11/1994 | European Pat. Off. |
| 3741910 | 6/1988 | Germany. |
| WO 95/00871 | 1/1995 | WIPO. |
| WO 96/27143 | 9/1996 | WIPO. |

OTHER PUBLICATIONS

Patent Abstracts of Japan, vol. 10, No. 183 (P–472), Jun. 26, 1986, "Microscope for Simultaneous Observation of Many Faces," (Abstract of Japanese Patent Publication No. 61032022 Feb. 14, 1986).

Hamilton, et al. "Three–Dimensional Surface Measurement Using the Confocal Scanning Microscope", Appl. Phys. B, 27: 211–213 (1982) (Month Unknown).

Engelhardt, et al. "Konfokale Laserscanning–Mikroskopie", Physik in unserer Zeit, 24 Jarg. 1993/Nr. 2, pp. 70–78 (Month Unknown).

Primary Examiner—Que T. Le
Attorney, Agent, or Firm—Foley & Lardner

[57] ABSTRACT

A system and method for simultaneous representation of a surface profile of any given object, specially to measure the surface profile of teeth, comprises a light source to illuminate the object, an optical element to focus the light signals returning from the surface of the object, a detector to pick up the light signals, and a processor that digitizes and further processes the detected signals. The method enables quick, reproducible scanning of the surface profile by using as few devices as possible while ensuring at the same time a viable constructive size. The method includes placing a beam output coupler in the beam detection path downstream from the optical element to simultaneously couple our the light returning from the various image planes, the coupled-out light being guided to the detector.

65 Claims, 7 Drawing Sheets

POLYFOCAL REPRESENTATION OF THE SURFACE PROFILE OF ANY GIVEN OBJECT

BACKGROUND OF THE INVENTION

The invention relates to an arrangement and to a method for simultaneous polyfocal imaging of the surface profile of any desired objects, in particular for measuring the surface profile of teeth, having a light source for illuminating the object, having optics for focusing the light signals returning from the surface of the object, having a detector which records the light signals, and having a processor which digitizes and further-processes the detected signals. The invention also relates to a particular application of the arrangement according to the invention for reading and writing digital or binary information from an optical data medium and, respectively, to an optical data medium.

In principle, the invention relates to an arrangement and to a method for measuring surfaces of any type and of any contour, to be precise using a technique known from confocal microscopy. Various arrangements and methods for surface measurement are already known from practical experience.

Thus, for example, a light section sensor can be used to project a light line onto the object, and a CCD camera can be used to observe it, at an angle. The geometrical deformation of the light line is in this case measured. The height differences on the object are calculated from this deformation. By shifting the object under the sensor—at right angles to the light line—and by repeatedly measuring a profile, the surface shape can be measured or determined in a serial manner.

The light section sensor is admittedly a sensor of simple design and is robust, but the oblique illumination required here leads to shadowing on one side of steep points. This results in asymmetries in the imaging and inaccuracies. Furthermore, the measurements are sometimes inaccurate or corrupted owing to light being scattered from various depths, for example, on at least partially transparent tooth material.

Furthermore, it is also already known from practical experience for surfaces to be scanned by means of confocal microscopy and for this to be used to generate three-dimensional records of the surface. For this purpose, reference is made, only by way of example, to J. Engelhardt and W. Knebel in "Konfokale Laserscanning-Mikroskopie" [Confocal laser scanning microscopy] Physik in unserer Zeit [Physics Today], Jan. 24, 1993, No. 2, pages 70–78 and D. K. Hamilton and T. Wilson in "Three-Dimensional Surface Measurement Using the Confocal Scanning Microscope" Applied Physics B,27: 211–213 (1982).

Confocal microscopy is particularly highly suitable for surface measurement of toothed surfaces since, according to this method, the only structures that are imaged are those which are located directly in the focal plane of the microscope objective. Measurement errors resulting from partially transparent tooth material are thus effectively prevented. However, conventional confocal microscopes corresponding to the prior art have a very considerable physical size owing to their universal nature, so that they are not suitable for polyfocal imaging of the surface profile of widely differing objects, for example for measuring the surface profile of teeth, owing to their physical size. Furthermore, conventional confocal microscopes have a design that is too complicated for numerous simple applications, such as pure profile measurement, and are thus much too expensive.

SUMMARY OF THE INVENTION

The present invention thus comprises an arrangement for simultaneous polyfocal imaging of the surface profile of any desired objects, and a corresponding method, according to which rapid and, at the same time, reproducible scanning of the surface profile is possible with an equipment cost that is as low as possible or is very low, while ensuring that the arrangement has an acceptable physical size.

The arrangement according to the invention for simultaneous polyfocal imaging of the surface profile of any desired objects, and in particular for measuring the surface profile of teeth, comprises an arrangement including a beam output coupler, which is arranged in a detection beam path downstream of optics and upstream of a detector, for simultaneously outputting the light returning from different image planes of the object, with the output light being supplied to the detector.

According to the invention, it has been identified here that, in principle, it is possible to at the same time output, from different image planes of the object, light returning from the object via optics, with the output light being supplied to the detector or to a plurality of detectors. The outputting may be carried out by means of a beam output coupler, which is arranged in the detection beam path downstream of the optics and upstream of the detector and which—as already stated—can at the same time output at a plurality of foci of the returning light, for simultaneous polyfocal imaging of the surface profile of the object. In this case, the object is simultaneously scanned in a plurality of focal planes, with the surface profile of the object being scanned overall.

In a particularly advantageous embodiment, the beam output coupler is arranged preferably centrally in the detection beam path and comprises deflection means at the respective focal points of the returning light. The deflection means are used to output the light toward the detector or toward the detectors. Specifically, the deflection means are arranged in series, seen in the beam direction, in the detection beam path, with the respective front deflection means masking out central regions of the entire beam of the returning light for the subsequent deflection means. Irrespective of this masking, the remaining light is still sufficient for it to be possible to mask out the returning light again at the next deflection means—in each case from another focal plane of the object.

In the context of a first embodiment, the beam output coupler could be designed as a translucent plate stack with plates arranged at a predetermined angle in series in the detection beam path and used as the deflection means. In this case, the translucent plates could be provided, at least in places, with a reflection layer so that, with the reflection layers arranged in an appropriate manner—in series roughly in the center of the detection beam path—the returning light is output from different focal planes in a stepped manner. In the context of this embodiment, it is in any case essential for the individual plates to be designed to be translucent and for reflection and outputting to take place only at the reflection layers provided in zones.

In the context of a further embodiment, the beam output coupler could be designed as a preferably monolithic plexi-glass module, with integral deflection means which are preferably arranged in series at a predetermined angle in the detection beam path. Such a plexiglass module, or the deflection means arranged integrally there, could be machined by milling, likewise with reflection layers being applied to the integral deflection means. These reflection layers reflect the returning light from different focal planes and output the light, corresponding to the foci, toward the detector.

It would likewise be feasible to design the beam output coupler as a series arrangement of pin holes. The returning light would then be masked out at, in each case, one pin hole in the region of a focal point, and would otherwise be reflected toward the next pin hole. The reflected element of the light would in turn be masked out in the region of a focal point, but would otherwise be reflected once again. A plurality of such pin holes can be arranged to communicate with one another, in which case it is possible to use mirrors which are arranged at a predetermined angle to reflect the respective light that is not output, and communicate with one another in the beam path. These mirrors define the pin holes (which are required for masking) as passages therethrough.

In the context of a further embodiment of the beam output coupler, this beam output coupler could comprise a housing or a light-conducting body. Both the housing and the light-conducting body would have to be arranged with an optical opening in the detection beam path of the returning light, specifically in order that the returning light can enter this optical opening. The incident light could be alternately reflected along two mutually opposite reflection surfaces, corresponding to the incidence angle, and be partially masked out toward the detectors at opposite pin holes at respective focal points—from corresponding focal planes of the object. The two opposite reflection surfaces could, in turn, be designed as mirror surfaces with pin holes formed therethrough.

Furthermore, it would be possible for the two opposite reflection surfaces to be designed to be exactly parallel to one another, in which case the reflection surfaces can, in principle, be walls of the housing or surfaces of a glass body or the like composed of solid material.

In the case of the housing or the light-conductive body, the two opposite reflection surfaces could become more remote from one another, that is, diverge, from the optical opening into the interior of the housing or body. To this extent, the space available for propagation of the light that has already been deflected would expand continuously or discontinuously. One of the two reflection surfaces could in this case be designed to be stepped, that is, to diverge from the opposite reflection surface in steps. Each of the surface elements produced in this way could in turn have a pin hole or a group of pin holes for masking out at light respective focal points.

Pin holes could likewise be provided in groups in the opposite reflection surfaces for simultaneous color splitting. Suitable detectors for recording the masked-out light can be arranged immediately adjacent to the pin holes or in the region of the pin holes. In this way, optical fibers, diodes or other detectors operating on an optical principle can be arranged on the sides of the arrangement opposite the reflection surfaces.

In the context of a further alternative, the beam output coupler could have a plurality of reflection surfaces arranged at a predetermined angle to one another, communicating with one another, and each reflection surface would have a pin hole. The reflection surfaces could form a polygonal arrangement overall. Once again, light is output at the pin holes at the respective focal points, and the output light is recorded by a detector.

The beam output coupler could likewise be designed as a slit system having a plurality of slits located alongside one another for parallel detection of the x- and z-coordinates of the returning light, so that simultaneous detection of a plurality of image points in a focal plane is possible.

Finally, optical fibers which end centrally at the respective focal points of the returning light could be preferably provided as the beam output coupler in the detection beam path, with the optical fibers supplying the output light to a photomultiplier. The essential feature here is likewise that a light output which is staggered at the respective focal points takes place in the beam path of the returning light, that the output light is supplied to a detector, and that analog or digital signal processing is connected downstream, among other reasons also for compensating for non-linear geometry effects, and possibly with interpolation for increased resolution.

Various detectors may be connected downstream of the beam output coupler, such as singular detectors, detector arrays, linear or area CCDs, diodes, photomultipliers, diode arrangements or position-sensitive diodes etc., in which case the beam output coupler and the detectors can be combined from the functional point of view, as well as to form assemblies.

If the beam output coupler and the detector are combined in a functional manner and to form an assembly, diodes could preferably be arranged centrally at the respective focal points of the returning light in the detection beam path, with these diodes operating as position-sensitive diodes owing to the fact that they are connected in series.

With regard to the illumination of the object, it is advantageous for polyfocal illumination to be used, for example by means of high spherical aberration, zone lenses, etc. In any case, the object is illuminated in a structured manner over a focal range which can be predetermined, in which case a laser light source may be used, for example, for polyfocal illumination. As already mentioned above, the polyfocal illumination can be produced by means of spherical aberration, zone lenses, holograms etc., with the light being focused onto different focal planes. The surface itself may be prepared on top with scattering or fluorescence means in order to allow quite particular effects to be used in the scattered or reflected light.

With regard to a method according to the invention, the method for simultaneous polyfocal imaging of the surface profile of any desired objects, in particular for measuring the surface profile of teeth, may include providing an arrangement having a light source for illuminating the object, having optics for focusing the light signals returning from the surface of the object, having a detector which records the light signals, and having a processor which digitizes and further-processes the detected signals.

The method according to the invention is characterized in that the light returning from different image planes is output from the detection beam path in the region downstream of the optics and upstream of the detector, and in that the output light is supplied to the detector, in which case the detector may be a singular detector, a detector arrangement or individual detectors. In the context of the present invention, it is highly advantageous for the object to be illuminated in a structured manner over a focal range which can be predetermined and, specifically, for the light to be focused onto different focal planes on the object. Specifically, polyfocal illumination of the object can be produced by spherical aberration, zone lenses, holograms or the like.

Finally, in a further manner according to the invention, the application of an arrangement according to the invention is claimed, using the method according to the invention, to be precise for reading digital or binary information from a plurality of levels in a three-dimensional optical data medium. A corresponding application is likewise claimed for writing digital or binary information to a plurality of levels in a three-dimensional optical data medium. In other words, the basic principle of polyfocal microscopy is intended to be used here, based on the outputting and detection principle involved here, on the one hand, for reading three-dimensional optical data memories, and, on the other hand, for writing to three-dimensional optical data memories, with the principle under discussion here being applicable irrespective of the amount of energy to be supplied.

BRIEF DESCRIPTION OF THE DRAWINGS

There are various options for refining and developing the teaching of the present invention in an advantageous manner. To this end, reference is made to the following explanation of various exemplary embodiments of the invention, with reference to the drawings. Preferred refinements and developments of the teaching are also explained in general in conjunction with the explanation of the preferred exemplary embodiments of the invention. In the drawings.

DETAILED DESCRIPTION OF THE PREFERRED EMBODIMENT

Figure 1:
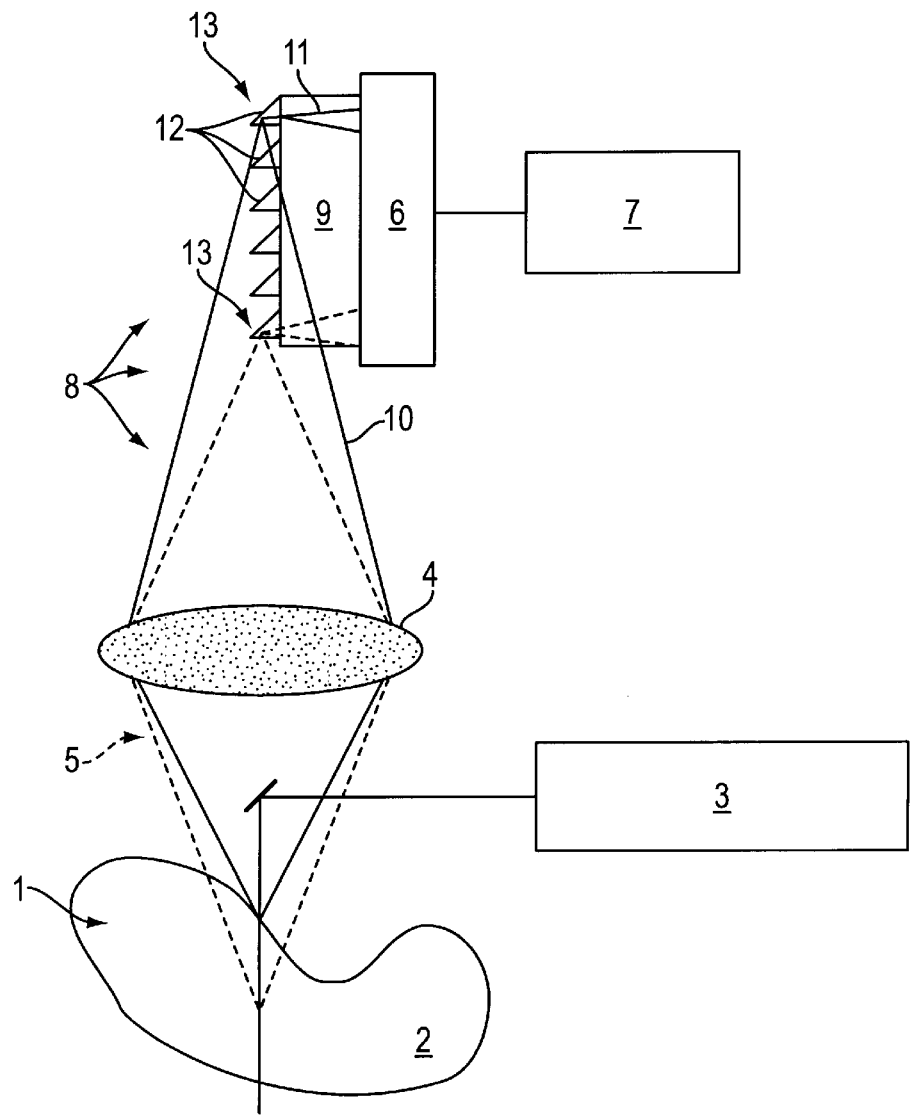
FIG. 1 shows a schematic illustration of a fundamental design of an arrangement according to the invention for simultaneous polyfocal imaging of the surface profile of any desired objects.
Figure 2:
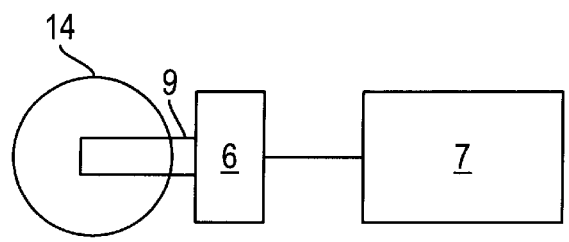
FIG. 2 shows a schematic illustration of a plan view of the arrangement from FIG. 1.

FIGS. 1 and 2 show, schematically, an arrangement for simultaneous polyfocal imaging of the surface profile 1 (which is only indicated here) of any desired objects 2, in which case this relates, in particular, to the measurement of the surface profile of teeth. The arrangement comprises a light source 3 for illuminating the object 2, optics 4 for focusing the light signals 5 returning from the surface 1 of the object 2, a detector 6 which records the light signals 5, and a processor 7 which digitizes and further-processes the detected signals.

According to the invention, a beam output coupler 9 is provided in the detection beam path 8, downstream of the optics 4 and upstream of the detector 6, and is used for simultaneously outputting the light 10 returning from different image planes of the object 2 and focused by the optics 4, with the output light 11 being supplied to the detector 6.

FIG. 1 furthermore shows that the beam output coupler 9 has deflection means 12, arranged centrally in the detection beam path 8, at the respective focal points 13 of the returning light 10. The deflection means 12 are arranged in series in the deflection beam path 8, with a respective front deflection means 12 masking out central regions of the entire beam 14 (illustrated schematically in FIG. 2) of the returning light 10 for a subsequent deflection means 12.

Figure 3:
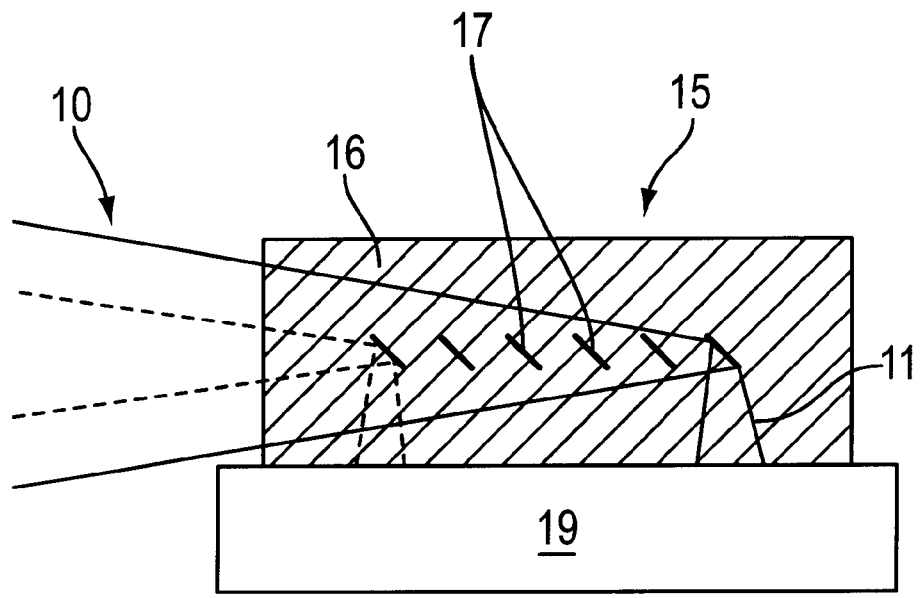
FIG. 3 shows a schematic illustration of an exemplary embodiment of a beam output coupler designed as a plate stack and having a detector array.

FIG. 3 shows a first exemplary embodiment of a beam output coupler 9 which can be used according to the invention and is designed, specifically, as a translucent plate stack 15 with plates 16 which are arranged at a predetermined angle in series in the detection beam path 8 and are used as deflection means 12. The translucent plates 16 are provided, in places, with reflection layers 17, which are in turn arranged in series in the detection beam path 8 and are used for outputting the returning light 10 at the respective focal points.

Figure 4:
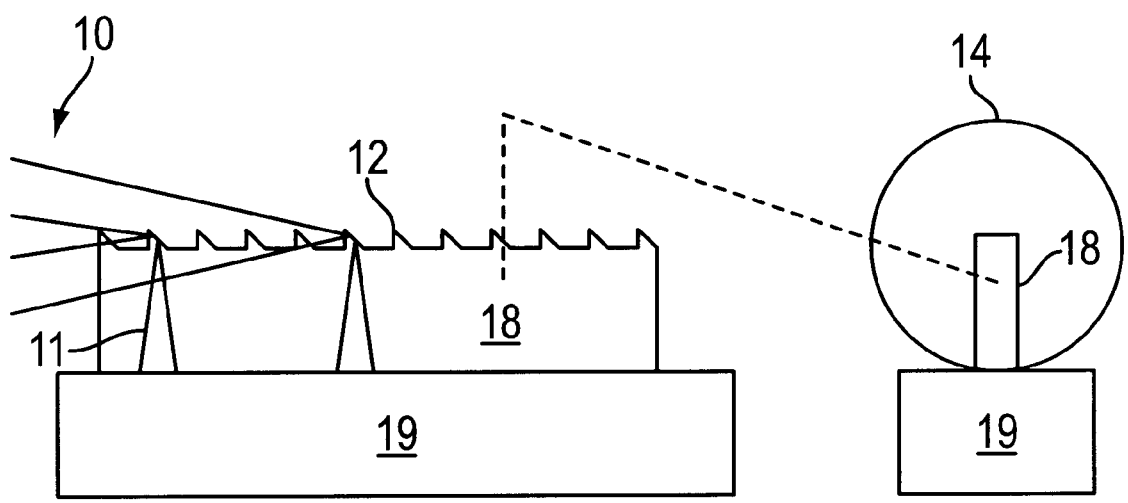
FIG. 4 shows a schematic illustration of a further exemplary embodiment of a beam output coupler, designed as a monolithic plexiglass block, as well as a detector array, to be precise in a side view on the left and in a plan view on the right.

According to the illustration in FIG. 4, the beam output coupler 9 is designed as a monolithic plexiglass module 18 having integral deflection means 12 arranged at a predetermined angle in series in the detection beam path 8. These deflection means 12 are also preferably provided with a reflection layer, which is not illustrated in FIG. 4. A detector array 19 is connected downstream of both the beam output coupler 9 as shown in FIG. 3 and the beam output coupler 9 as shown in FIG. 4, in which case these may likewise be position-sensitive diodes.

Figure 5:
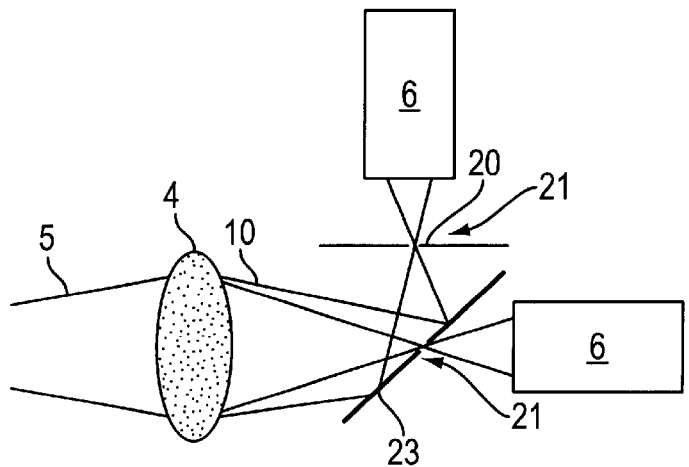
FIG. 5 shows a schematic illustration of a further option for beam outputting by connecting mirrors, as well as pin holes, together with detectors in series.
Figure 6:
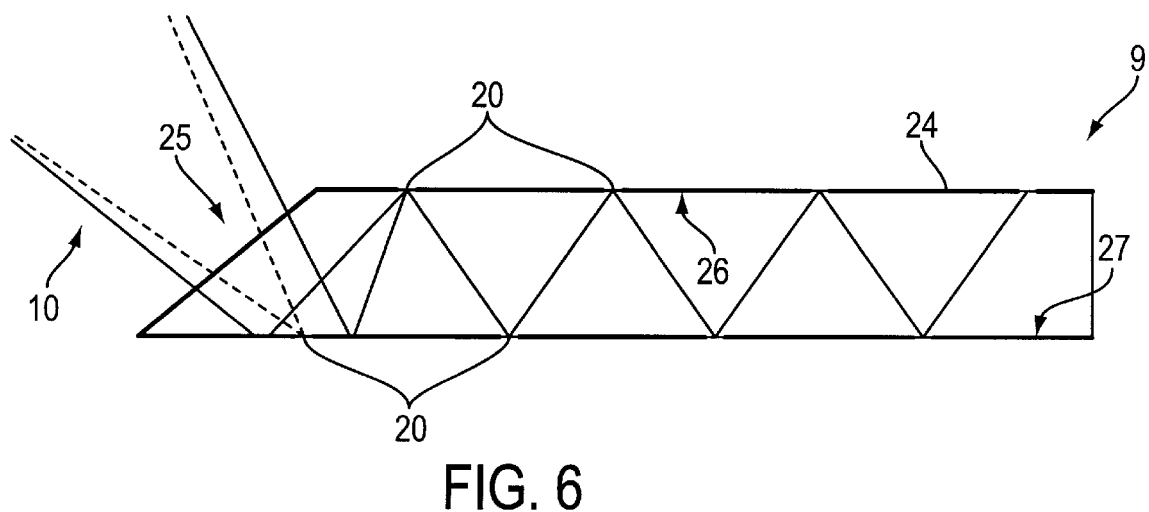
FIG. 6 shows a schematic illustration of a beam output coupler having two opposite reflection surfaces.
Figure 7:
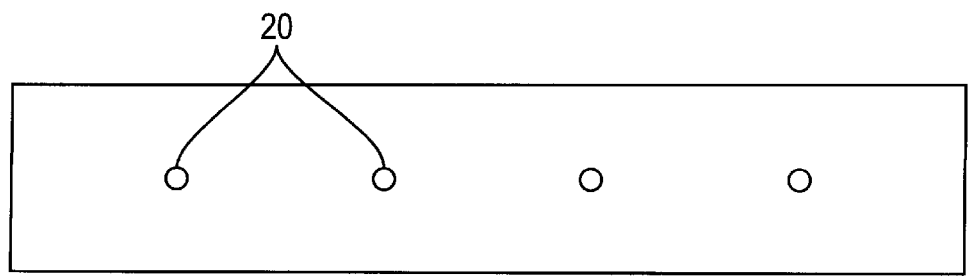
FIG. 7 shows a schematic illustration of the subject matter from FIG. 6, in plan view, of the pin holes which are used for beam output coupling.
Figure 8:
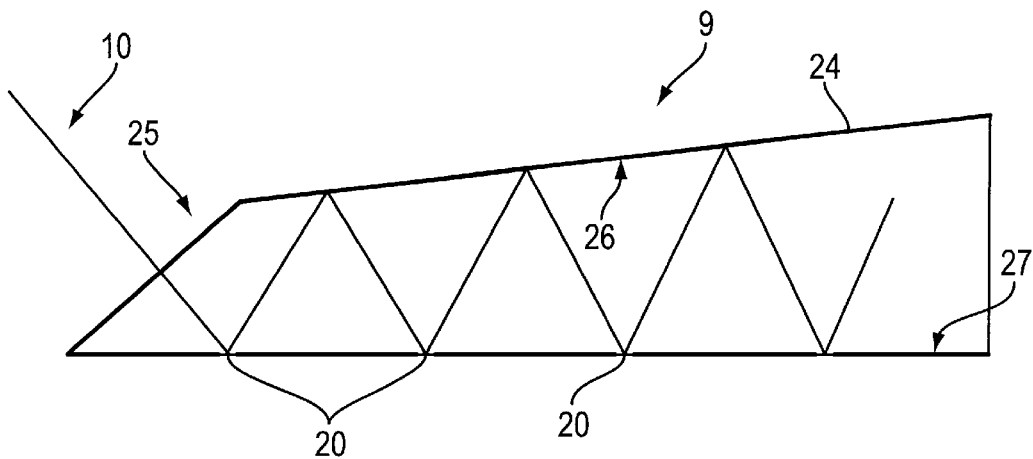
FIG. 8 shows a schematic illustration of a further exemplary embodiment of the beam output coupler as shown in FIG. 6, but with diverging opposite reflection surfaces.

FIG. 5 shows a further exemplary embodiment of a beam output coupler 9 which, specifically, is designed as a series arrangement of pin holes 20. The returning light 10 is in this case masked out at a pin hole 20 in the region of a focal point 21, and is otherwise reflected toward the next pin hole 20. The reflected element of the light 22 is in turn masked out in the region of a focal point 21, and is otherwise reflected once again. This process can be repeated a number of times, so that a number of masking operations take place in cascaded form. According to the exemplary embodiment chosen here, the light which is not output in each case is reflected by means of mirrors 23 which communicate with one another, and is in each case masked out at the pin hole 20 formed there.

According to FIGS. 6 to 10, the beam output coupler 9 may comprise a housing 24 or a light-conductive body which has an optical opening 25 (which can be arranged centrally in the detection beam path 8) for the returning light 10, which is incident at a specific angle. The incident light 10 is in this case reflected alternately along two mutually opposite reflection surfaces 26, 27, corresponding to the incidence angle, and is partially masked out at opposite pin holes 20 at the respective focal point 21 for the detectors, which are not shown in FIGS. 6 to 10. A particular illustration of individual detectors has been dispensed with here only to assist clarity.

Specifically, the two mutually opposite reflection surfaces 26, 27 are designed as mirror surfaces with pin holes 20 formed in them. According to the exemplary embodiment shown in FIG. 6, the two opposite reflection surfaces 26, 27 are designed to be parallel to one another. In the exemplary embodiment illustrated in FIG. 8, only the reflection surface 27 has pin holes 20, and the two reflection surfaces 26, 27 diverge from the optical opening 25 into the interior of the housing 24.

Figure 9:
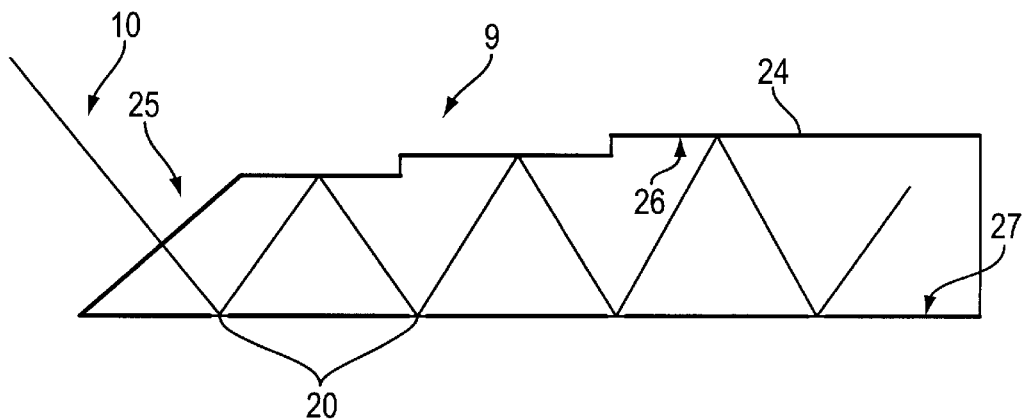
FIG. 9 shows a schematic illustration of a further exemplary embodiment of a beam output coupler having two opposite reflection surfaces, with one of the reflection surfaces being stepped.

In the case of the exemplary embodiment illustrated in FIG. 9, the reflection surface 26 is designed to be stepped and becomes more remote from the opposite reflection surface 27 from the optical opening 25 into the interior of the housing 24, in which case, once again, only the reflection surface 27 has pin holes 20.

Figure 10:
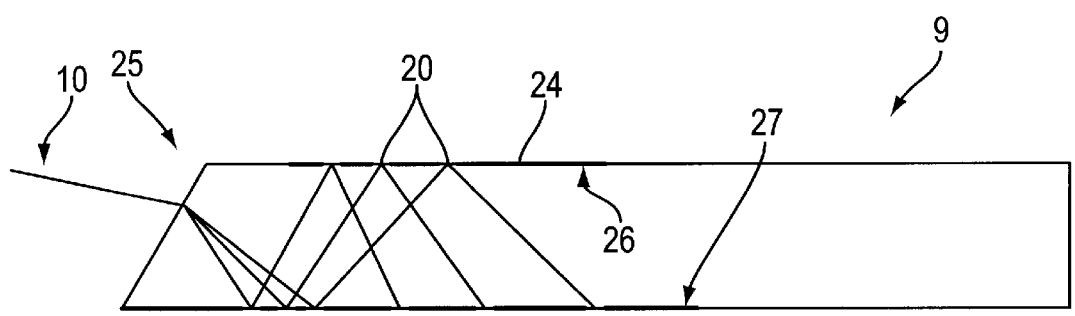
FIG. 10 shows a schematic illustration of a further exemplary embodiment of a beam output coupler having two opposite reflection surfaces, with pin holes being provided in groups for simultaneous color splitting.

In the case of the exemplary embodiment shown in FIG. 10, pin holes 20 are provided in groups, for simultaneous color splitting, in the opposite reflection surfaces 26, 27.

Figure 11:
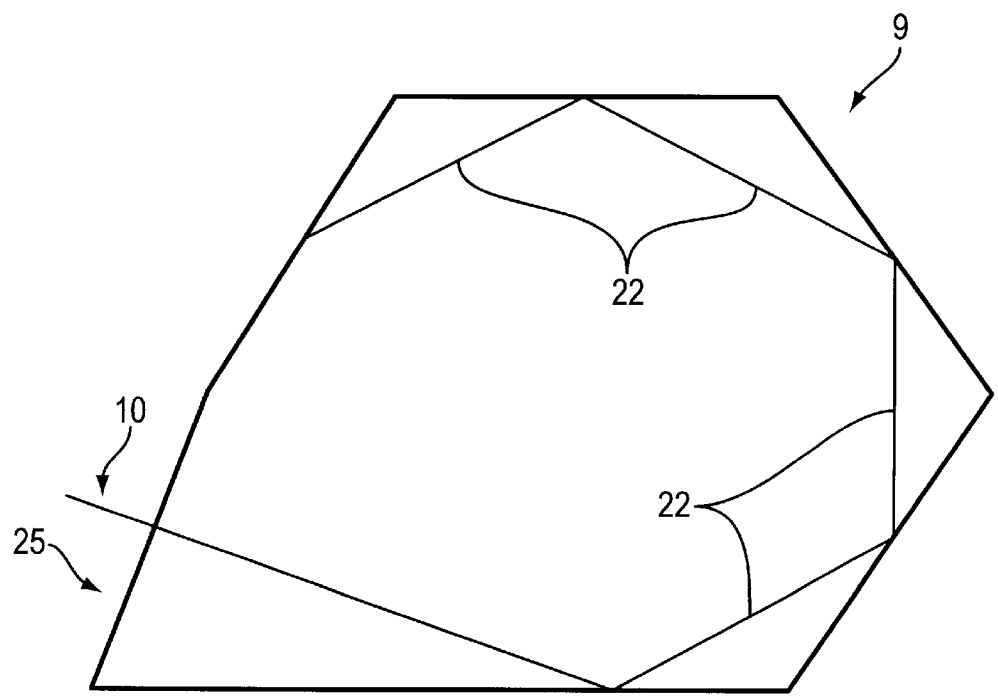
FIG. 11 shows a schematic illustration of a further exemplary embodiment of a beam output coupler having reflection surfaces in a polygonal arrangement.

According to the illustration in FIG. 11, the beam output coupler 9 is designed in the sense of a polygonal arrangement; specifically, it has a plurality of reflection surfaces 26 which are arranged at a predetermined angle to one another and communicate with one another, and in which pin holes 20 are once again formed. Light which is not masked out is reflected on the reflection surfaces 26 and passes, as the reflecting element of the light 22, to the respective next pin hole 20.

Figure 12:
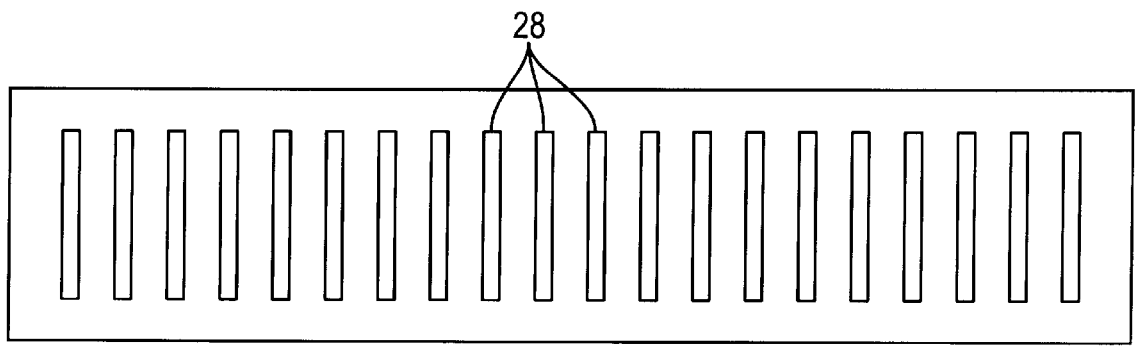
FIG. 12 shows a schematic illustration of a beam output coupler designed as a slit system.

A further exemplary embodiment of a beam output coupler 9 is shown in FIG. 12. Specifically, this beam output coupler 9 is designed as a slit system having a plurality of slits 28, located alongside one another, for parallel detection of the x- and z-coordinates of the returning light, so that simultaneous detection of a plurality of image points in one focal plane is possible.

Figure 13:
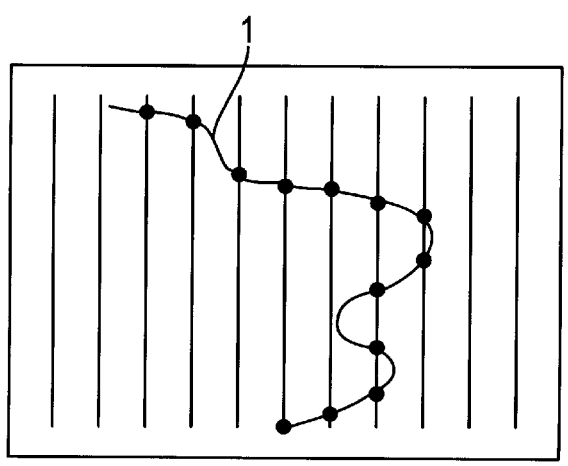
FIG. 13 shows a schematic illustration of slit-by-slit imaging of the object by means of a 2D-camera or with a Y-scan.

FIG. 13 shows a corresponding illustration of the slits 28 by means of a 2D-camera in real-time profile measurements, in which case such an arrangement may also be produced using a Y-scan. A three-dimensional data record can be produced with 50 cuts per second (video) in about one second.

Figure 14:
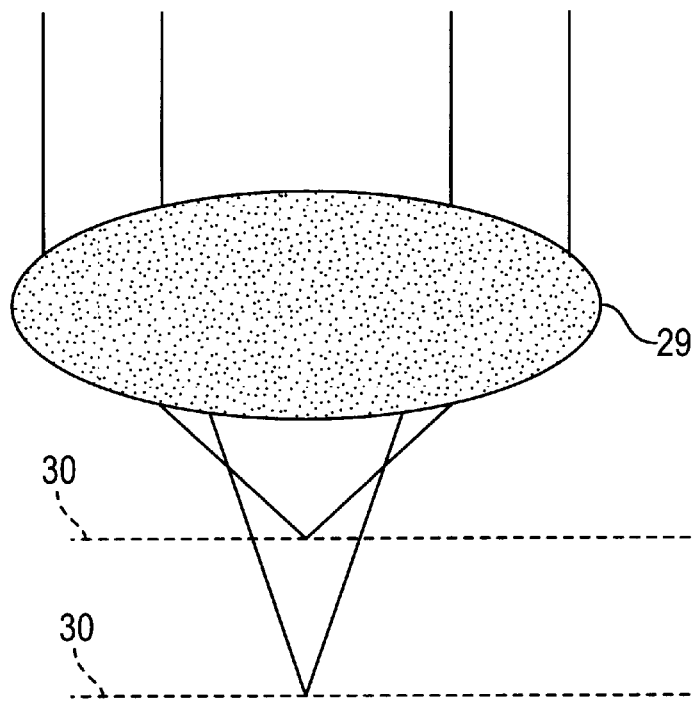
FIG. 14 shows a schematic illustration of an exemplary embodiment of an arrangement for polyfocal illumination of the object.
Figure 15:
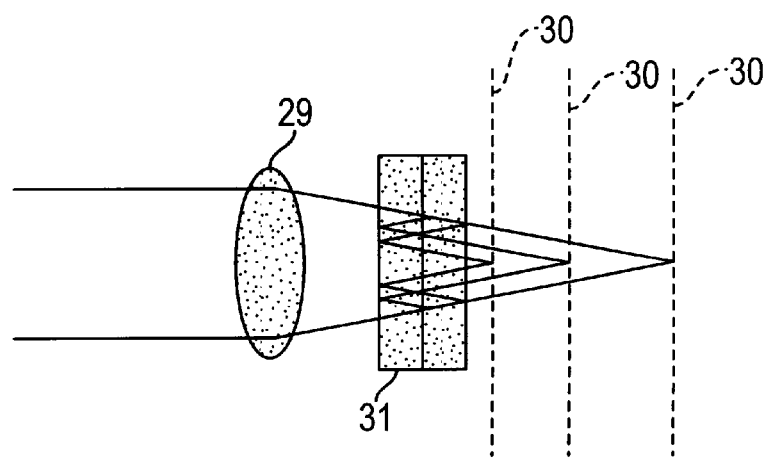
FIG. 15 shows a schematic illustration of a further exemplary embodiment for polyfocal illumination.

Finally, FIGS. 14 and 15 relate to the polyfocal illumination of the object 2, for which purpose a laser light source may be provided. In any case, the polyfocal illumination can be achieved, for example, by means of a zone lens 29 (which is only indicated in FIG. 14), in which case the light is focused onto various focal planes 30. FIG. 15 likewise relates to the possibility of polyfocal illumination, in which the light is focused onto various focal planes 30 for structured illumination, to be precise by means of a multiple reflection plate 31, by which means a plurality of focal points in a plurality of focal planes 30 are likewise achieved.

With regard to the applications (which are likewise claimed) of the arrangement discussed above, reference is made to the general description, in order to avoid repetitions.

| List of reference symbols | |
|---|---|
| 1 | Surface profile, surface |
| 2 | Object |
| 3 | Light source |
| 4 | Optics |
| 5 | Returning light signal |
| 6 | Detector |
| 7 | Processor |
| 8 | Detection beam path |
| 9 | Beam output coupler |
| 10 | Focused, returning light |
| 11 | Output light |
| 12 | Deflection means |
| 13 | Focal point of the returning light |
| 14 | Entire beam (FIG. 2) |
| 15 | Plate stack |
| 16 | Plate |
| 17 | Reflection layer |
| 18 | Plexiglass module |
| 19 | Detector array |
| 20 | Pin hole |
| 21 | Focal point |
| 22 | Reflected element of the light |
| 23 | Mirror |
| 24 | Housing |
| 25 | Optical opening |
| 26 | Reflection surface |
| 27 | Reflection surface |
| 28 | Slit |
| 29 | Zone lens |
| 30 | Focal plane |
| 31 | Multiple reflection plate |

What is claimed is:

1. A system for the simultaneous polyfocal imaging of a surface profile of any object, comprising:
   a light source for illuminating the object;
   at least one optical element for focusing light signals returning from the surface of the object;
   a detector for detecting the light signals;
   a processor for digitizing and processing the detected light signals; and
   a beam output coupler for simultaneously separating light returning from different image planes of the object and feeding the separated light to the detector, the beam output coupler being arranged in a detection beam path downstream of the optical element, the beam output coupler being configured as an arrangement of at least two pin holes in series,
   wherein the beam output coupler defines a first pin hole located at a first focal point and a second pin hole located next in the series at a second focal point, and
   wherein a first portion of the light returning from the different image planes is masked out at the first pin hole and the light remaining is reflected to the second pin hole, and
   wherein a portion of the reflected light is masked out at the second pin hole and the light remaining is reflected.

2. A system according to claim 1, wherein the beam output coupler comprises at least two mirrors, one defining the first pin hole and the other defining the second pin hole, the mirrors being arranged at a predetermined angle relative to each other to reflect light that has not been masked out at the one mirror by the first pin hole to the other mirror.

3. A system according to claim 1, wherein the detector comprises a detector array positioned downstream of the beam output coupler.

4. A system according to claim 1, wherein the detector comprises diodes positioned downstream of the beam output coupler.

5. A system according to claim 1, wherein the detector comprises diodes provided at the first and second focal points of the returning light, the diodes operating as position-sensitive diodes.

6. A system according to claim 1, wherein the light source illuminates the object over a predetermined focal range.

7. A system according to claim 1, wherein the light source comprises a laser light source.

8. A system according to claim 1, wherein polyfocal illumination is produced by at least one of spherical aberration, zone lenses, and holograms, wherein light is focused on different focal planes.

9. A system for the simultaneous polyfocal imaging of a surface profile of any object, comprising:
   a light source for illuminating the object;
   at least one optical element for focusing light signals returning from the surface of the object;
   a detector for detecting the light signals;
   a processor for digitizing and processing the detected light signals; and
   a beam output coupler for simultaneously separating light returning from different image planes of the object and feeding the separated light to the detector, the beam output coupler being arranged in the detection beam path downstream of the optical element, the beam output coupler being configured as an arrangement of pin holes in series, each located at a focal point, a portion of the light returning from the different image planes being masked out at a pin hole located at the focal point of that portion of the light, and the light remaining being reflected to the next-in-series pin hole.

10. A system according to claim 9, wherein the beam output coupler comprises mirrors, each mirror defining one of the pin holes, the mirrors being arranged at predetermined angles relative to each other to reflect light that has not been masked out at one mirror by a respective pin hole to another mirror located next in the series.

11. A system according to claim 9, wherein the detector comprises a plurality of detectors, each associated with a respective one of the pin holes for detecting the light that is masked out by the respective pin hole.

12. A system according to claim 9, wherein the detector comprises diodes provided at respective focal points of the returning light, the diodes operating as position-sensitive diodes.

13. A system according to claim 9, wherein the light source illuminates the object over a predetermined focal range.

14. A system according to claim 9, wherein the light source comprises a laser light source.

15. A system according to claim 9, wherein polyfocal illumination is produced by at least one of spherical aberration, zone lenses, and holograms, wherein light is focused on different focal planes.

16. A system according to claim 9, wherein the beam output coupler includes optical fibers that terminate at respective focal points of the returning light.

17. A system according to claim 9, wherein the optical fibers supply output light to a photomultiplier.

18. A system for the simultaneous polyfocal imaging of the surface profile of any object, comprising:
   a light source for illuminating the object;
   at least one optical element for focusing light signals returning from the surface of the object;
   a detector for detecting the light signals;
   a processor for digitizing and processing the detected light signals; and
   a beam output coupler for simultaneously separating light returning from different image planes of the object and feeding the separated light to the detector, the beam output coupler being arranged in the detection beam path downstream of the optical element, the beam output coupler comprising a housing having two opposed reflection surfaces and an optical opening located in the detection beam path of the returning light,
   wherein the returning light is alternately reflected, according to an angle of incidence of the returning light, along the two opposed reflection surfaces, each defining at least one pin hole therethrough located at a respective focal point of the returning light for masking out a portion of the returning light associated with the respective focal point.

19. A system according to claim 18, wherein the two opposed reflection surfaces are mirror surfaces.

20. A system according to claim 18, wherein the two opposed reflection surfaces are parallel to one another.

21. A system according to claim 18, wherein the two opposed reflection surfaces diverge from each other in a direction from the optical opening to an interior of the housing.

22. A system according to claim 18, wherein one of the two opposed reflection surfaces has a stepped configuration and becomes more remote from the other of the two opposed reflection surfaces in a direction from the optical opening to an interior of the housing.

23. A system according to claim 22, wherein the one of the two opposed reflection surfaces has a pin hole in each stepped segment.

24. A system according to claim 18, wherein the two opposed reflection surfaces each have a plurality of pin holes, and the pin holes are grouped for simultaneous color splitting.

25. A system according to claim 18, wherein the beam output coupler includes optical fibers that terminate at respective focal points of the returning light.

26. A system according to claim 25, wherein the optical fibers supply output light to a photomultiplier.

27. A system according to claim 18, wherein the housing comprises a light-conducting body.

28. A system according to claim 18, wherein the optical opening is disposed centrally in the detection beam path.

29. A system according to claim 18, wherein the pin holes in the two opposed reflection surfaces are located opposite each other.

30. A system according to claim 18, wherein the detector comprises a detector array positioned downstream of the beam output coupler.

31. A system according to claim 18, wherein the detector comprises diodes positioned downstream of the beam output coupler.

32. A system according to claim 18, wherein the detector comprises diodes provided at respective focal points of the returning light, the diodes operating as position-sensitive diodes.

33. A system according to claim 18, wherein the light source illuminates the object over a predetermined focal range.

34. A system according to claim 18, wherein the light source comprises a laser light source.

35. A system according to claim 18, wherein polyfocal illumination is produced by at least one of spherical aberration, zone lenses, and holograms, wherein light is focused on different focal planes.

36. A system for the simultaneous polyfocal imaging of a surface profile of any object, comprising:
- a light source for illuminating the object;
- at least one optical element for focusing light signals returning from the surface of the object;
- a detector for detecting the light signals;
- a processor for digitizing and processing the detected light signals; and
- a beam output coupler for simultaneously separating light returning from different image planes of the object and feeding the separated light to the detector, the beam output coupler being arranged in the detection beam path downstream of the optical element, the beam output coupler having a polygonal shape and a plurality of reflecting surfaces arranged at predetermined angles relative to one another, each of the reflecting surfaces having at least one pin hole.

37. A system according to claim 36, wherein the beam output coupler includes optical fibers that terminate at respective focal points of the returning light.

38. A system according to claim 37, wherein the optical fibers supply output light to a photomultiplier.

39. A system according to claim 36, wherein the detector comprises a detector array positioned downstream of the beam output coupler.

40. A system according to claim 36, wherein the detector comprises diodes positioned downstream of the beam output coupler.

41. A system according to claim 36, wherein the detector comprises diodes provided at respective focal points of the returning light, the diodes operating as position-sensitive diodes.

42. A system according to claim 36, wherein the light source illuminates the object over a predetermined focal range.

43. A system according to claim 36, wherein the light source comprises a laser light source.

44. A system according to claim 36, wherein polyfocal illumination is produced by at least one of spherical aberration, zone lenses, and holograms, wherein light is focused on different focal planes.

45. A system for the simultaneous polyfocal imaging of a surface profile of any object, comprising:
- a light source for illuminating the object;
- at least one optical element for focusing light signals returning from the surface of the object;
- a detector for detecting the light signals;
- a processor for digitizing and processing the detected light signals; and
- a beam output coupler for simultaneously separating light returning from different image planes of the object and feeding the separated light to the detector, the beam output coupler being arranged in the detection beam path downstream of the optical element, the beam output coupler defining a plurality of slits located alongside one another for parallel detection of x- and z-coordinates of the returning light to permit simultaneous detection of several image points in one focal plane.

46. A system according to claim 45, wherein the beam output coupler includes optical fibers that terminate at respective focal points of the returning light.

47. A system according to claim 45, wherein the optical fibers supply output light to a photomultiplier.

48. A system according to claim 45, wherein the detector comprises a detector array positioned downstream of the beam output coupler.

49. A system according to claim 45, wherein the detector comprises diodes positioned downstream of the beam output coupler.

50. A system according to claim 45, wherein the detector comprises diodes provided at respective focal points of the returning light, the diodes operating as position-sensitive diodes.

51. A system according to claim 45, wherein the light source illuminates the object over a predetermined focal range.

52. A system according to claim 45, wherein the light source comprises a laser light source.

53. A system according to claim 45, wherein polyfocal illumination is produced by at least one of spherical aberration, zone lenses, and holograms, wherein light is focused on different focal planes.

54. A method for simultaneous polyfocal imaging of the surface profile of any desired objects, comprises:
- providing an arrangement including a light source for illuminating the object, at least one optical element for focusing light signals returning from the surface of the object, a detector for detecting the light signals, a processor for digitizing and processing the detected light signals, and a beam output coupler for simultaneously separating light returning from different image planes of the object and feeding the separated light to the detector, the beam output coupler being arranged in the detection beam path downstream of the optical element, the beam output coupler being configured as an arrangement of pin holes in series, each located at a focal point, a portion of the light returning from the different image planes being masked out at a pin hole located at the focal point of that portion of the light, and the light remaining being reflected to the next-in-series pin hole;
- outputting from the detection beam path the light returning from different image planes in a region downstream of the optics and upstream of the detector; and
- supplying the output light to the detector.

55. A method according to claims 54, further comprising reading digital or binary information from a plurality of levels in a three-dimensional optical data medium.

56. A method according to claim 54, further comprising writing digital or binary information from a plurality of levels in a three-dimensional optical data medium.

57. A method for simultaneous polyfocal imaging of the surface profile of any desired objects, comprises:
- providing an arrangement including a light source for illuminating the object, at least one optical element for focusing light signals returning from the surface of the object, a detector for detecting the light signals, a processor for digitizing and processing the detected light signals, and a beam output coupler for simultaneously separating light returning from different image planes of the object and feeding the separated light to the detector, the beam output coupler being arranged in the detection beam path downstream of the optical element, the beam output coupler comprising a housing having two opposed reflection surfaces and an optical opening located in the detection beam path of the returning light,
- wherein the returning light is alternately reflected, according to an angle of incidence of the returning light, along the two opposed reflection surfaces, each defining at least one pin hole therethrough located at a respective focal point of the returning light for masking out a portion of the returning light associated with the respective focal point;

outputting from the detection beam path the light returning from different image planes in a region downstream of the optics and upstream of the detector; and supplying the output light to the detector.

58. A method according to claim 57, further comprising reading digital or binary information from a plurality of levels in a three-dimensional optical data medium.

59. A method according to claim 57, further comprising writing digital or binary information from a plurality of levels in a three-dimensional optical data medium.

60. A method for simultaneous polyfocal imaging of the surface profile of any desired objects, comprises:

providing an arrangement including a light source for illuminating the object, at least one optical element for focusing light signals returning from the surface of the object, a detector for detecting the light signals, a processor for digitizing and processing the detected light signals, and a beam output coupler for simultaneously separating light returning from different image planes of the object and feeding the separated light to the detector, the beam output coupler being arranged in the detection beam path downstream of the optical element, the beam output coupler having a polygonal shape and a plurality of reflecting surfaces arranged at a predetermined angle relative to one another, each of the reflecting surfaces having at least one pin hole;

outputting from the detection beam path the light returning from different image planes in a region downstream of the optics and upstream of the detector; and supplying the output light to the detector.

61. A method according to claim 60, further comprising reading digital or binary information from a plurality of levels in a three-dimensional optical data medium.

62. A method according to claim 60, further comprising writing digital or binary information from a plurality of levels in a three-dimensional optical data medium.

63. A method for simultaneous polyfocal imaging of the surface profile of any desired objects, comprises:

providing an arrangement including a light source for illuminating the object, at least one optical element for focusing light signals returning from the surface of the object, a detector for detecting the light signals, a processor for digitizing and processing the detected light signals, and a beam output coupler for simultaneously separating light returning from different image planes of the object and feeding the separated light to the detector, the beam output coupler being arranged in the detection beam path downstream of the optical element, the beam output coupler defining a plurality of slits located alongside one another for parallel detection of x- and z-coordinates of the returning light to permit simultaneous detection of several image points in one focal plane;

outputting from the detection beam path the light returning from different image planes in a region downstream of the optics and upstream of the detector; and supplying the output light to the detector.

64. A method according to claim 63, further comprising reading digital or binary information from a plurality of levels in a three-dimensional optical data medium.

65. A method according to claim 63, further comprising writing digital or binary information from a plurality of levels in a three-dimensional optical data medium.

* * * * *